United States Patent
Lee (10) Patent No.: US 11,564,961 B2
(45) Date of Patent: *Jan. 31, 2023

(54) PREPARATION METHOD OF A CANNABIS EXTRACT COMPOSITION FOR REDUCTION OF SIDE EFFECTS OF ANTICANCER TREATMENT, OR CANCER METASTASIS SUPPRESSION

(71) Applicant: FAMENITY CO., LTD., Uiwang-si (KR)

(72) Inventor: Ji Won Lee, Gwacheon-si (KR)

(73) Assignee: FAMENITY CO., LTD., Uiwang-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/516,595

(22) Filed: Nov. 1, 2021

(65) Prior Publication Data

US 2022/0047662 A1 Feb. 17, 2022

Related U.S. Application Data

(63) Continuation of application No. 16/778,073, filed on Jan. 31, 2020, now abandoned.

(51) Int. Cl.
- *A61K 36/185* (2006.01)
- *A61K 9/00* (2006.01)
- *A61P 35/00* (2006.01)

(52) U.S. Cl.
CPC .......... *A61K 36/185* (2013.01); *A61K 9/0014* (2013.01); *A61K 9/0095* (2013.01); *A61P 35/00* (2018.01); *A61K 2236/333* (2013.01)

(58) Field of Classification Search
None
See application file for complete search history.

(56) References Cited

FOREIGN PATENT DOCUMENTS

JP 2003146844 * 5/2003

* cited by examiner

*Primary Examiner* — Michael V Meller
(74) *Attorney, Agent, or Firm* — STIP Law Group, LLC (57) ABSTRACT

The present invention relates to a method of making a cannabis extract composition comprising a cannabis extract as an active ingredient to reduce anti-cancer side effects and suppress cancer metastasis during internal use and administration by suppressing the activity of MMP-2 and MMP-9.

1 Claim, 2 Drawing Sheets

PREPARATION METHOD OF A CANNABIS EXTRACT COMPOSITION FOR REDUCTION OF SIDE EFFECTS OF ANTICANCER TREATMENT, OR CANCER METASTASIS SUPPRESSION

CROSS-REFERENCE TO RELATED APPLICATIONS

This application is a Continuation of U.S. application Ser. No. 16/778,073 filed on Jan. 31, 2020, the disclosures of which are incorporated by reference into the present application.

TECHNICAL FIELD

The present invention relates to a preparation method of a cannabis extract composition for anti-cancer, reducing anti-cancer side effects and suppressing cancer metastasis, including a cannabis extract as an active ingredient. More particularly, the present invention relates to a composition for anti-cancer, reducing anti-cancer side effects and suppressing cancer metastasis, which decreases the rate of cancer metastasis, is excellent in reducing the viability of cancer cells, does not have side effects caused by internal use and administration of the composition, and does not cause cancer to be resistant, using a cannabis extract.

BACKGROUND ART

Cancer shows a high mortality rate worldwide, and is the second most common cause of death next to cardiovascular diseases in western societies. In particular, lung cancer is increasing due to an increase in the smoking population and air pollution along with the aging of the population, the intake of high-fat diets has become common due to westernized eating habits, and colorectal cancer, breast cancer, prostate cancer, and the like tend to increase continuously due to a rapid increase in environmental pollutants, an increase in alcohol consumption, and the like. Under such circumstances, there is an urgent need for creating anti-cancer substances capable of contributing to the promotion of human health, the improvement in the quality of healthy life, and the promotion of public health by enabling cancer to be prevented and treated.

Malignant tumors spread from one organ, the primary site of occurrence, to other tissues after the development in one organ (the lungs, liver, kidneys, stomach, large intestine, rectum, and the like) in most cases, and spread from the primary site of tumor to other tissues is called metastasis.

Metastasis is a phenomenon accompanied by the progression of a malignant tumor, and after malignant tumor cells proliferate and acquire new genetic traits required for metastasizing as the cancer progresses, the malignant tumor cells infiltrate the blood vessels and lymph glands, circulate along the blood and lymph, settle and then proliferate in other tissues. Recent studies have revealed genetic traits associated with metastasis, and genetic testing of the primary tissue may be used to infer a recurrence high-risk group via metastasis to other organs in the future.

Treatment of metastasis of malignant tumors may be divided into local treatment and systemic treatment, and the principle of treatment of metastasis of malignant tumors differs depending on the type of tumor and the tumor metastasis site. In the case of some malignant tumors whose local symptoms become severe due to metastasis, or a surgical treatment of metastasis is known to be capable of modulating the natural course of malignant tumors, local treatment strategies such as therapeutic surgery or radiation therapy may be considered for metastasis. In general, when metastasis occurs from a malignant tumor, it is helpful to treat the tumor not only at the metastatic site but also at the primary site together through systemic treatment such as anti-cancer chemotherapy rather than local treatment. However, except for a very small number of tumors, such as lymphoma, malignant tumors where metastasis occurs are rarely cured completely.

The course of malignant tumors where metastasis occurs varies, and is determined depending on the type of primary malignant tumor and the overall tumor progression rate. Complications may vary depending on which organ the malignant tumor has metastasized to. For example, in the case of brain metastasis, symptoms such as headache, visual field loss, and vomiting may occur. In the case of bone metastasis, bone pain may occur, and pathological fracture may occur. Mental fog may also occur due to hypercalcemia accompanied by bone metastasis. Accordingly, early detection of tumor through diagnosis and genetic testing of the primary tumor are methods of preventing an increase in mortality rate from metastasis.

Drugs developed for treating cancer to date are a systemic injection or orally administered drug, and act non-specifically on the whole body along the bloodstream and have low specificity for cancer cells, and have a disadvantage in that many side effects occur compared to surgery and radiation therapy because there are many systemic side effects due to administration of the drug. Meanwhile, no breakthrough drug has been developed, which can prevent cancer cells from metastasizing to other organs without showing cell toxicity.

Cancer pain is a pain caused by the cancer disease itself or treatment, and is experienced by many patients who are currently being treated and patients with advanced cancer.

Cancer pain depends on various factors including the type of cancer, the stage of the disease, the site of the disease and the patient's resistance to the pain, and cancer pain may be from the primary cancer itself or from other sites of the body where the cancer has spread (metastasized). As the tumor grows, the cancer may exert pressure on nerves, bones, or other organs, which may cause pain. Pain may also be caused by bone fracture, disease-related infection or inflammation. Cancer pain may be caused not only by the physical consequences of cancer at body sites, but also by chemicals secreted from cancer cells and tissues. The type of cancer pain may also be various. For example, cancer pain may be acute, chronic, or breakthrough pain. Cancer pain may also change during each pain period, and the severity and frequency of pain may also vary.

Therefore, the control of pain in patients with cancer needs to be performed in order for the patients to be able to carry out their daily life.

The two main drug classes used to treat cancer pain are opioid analgesics and non-steroidal anti-inflammatory drugs (NSAIDs). These classes of drugs are typically administered systemically. Systemic drug administration to reduce cancer pain is often problematic. For example, systemic administration of opioids for cancer pain may cause nausea, suppression of bowel function, urine stagnation, suppression of lung functions, cardiovascular effects and sedative action, and may cause undesired central nervous system-mediated side effects, deterioration in respiratory functions, sedative action, and drowsiness.

Therefore, there is a need for a composition free from side effects even when the composition is systemically administered as an effect capable of preventing the metastasis of cancer cells to other organs.

PRIOR ART DOCUMENT

Patent Document (Patent Document 1) KR 10-2015-0003111 A

SUMMARY OF THE INVENTION

The present invention has been made in an effort to provide a composition for anti-cancer, reducing anti-cancer side effects and suppressing cancer metastasis, including a cannabis extract as an active ingredient.

The present invention has also been made in an effort to provide a composition for anti-cancer, reducing anti-cancer side effects and suppressing cancer metastasis, which shows effects of a cannabis extract of suppressing terminal cancer metastasis and reducing the viability of cancer cells.

The present invention has also been made in an effort to provide a composition for anti-cancer, reducing anti-cancer side effects and suppressing cancer metastasis, which is excellent in effects of suppressing cancer metastasis and reducing the viability of cancer cells, does not have side effects during the internal use and administration of the composition, and does not cause cancer to be resistant.

An exemplary embodiment of the present invention provides a composition for anti-cancer, reducing anti-cancer side effects, and suppressing cancer metastasis according to an exemplary embodiment of the present invention includes a cannabis extract as an active ingredient.

The cannabis extract includes cannabinoids and terpene.

The cancer includes those selected from the group consisting of thyroid cancer, lung cancer, gastric cancer, liver cancer, colorectal cancer, pancreatic cancer, prostate cancer, uterine cancer, breast cancer, and skin cancer.

The composition shows effects of suppressing terminal cancer metastasis and reducing the viability of cancer cells.

The cannabis extract includes those that suppress the activity of MMP-2 and MMP-9 to decrease the rate of cancer metastasis.

The extract includes those extracted using an extraction solvent selected from the group consisting of water, $C_1$ to $C_6$ lower alcohols, and a mixture thereof.

A functional food according to another exemplary embodiment of the present invention is prepared using a composition for anti-cancer, reducing anti-cancer side effects and suppressing cancer metastasis, including a cannabis extract as an active ingredient.

A skin external preparation according to still another exemplary embodiment of the present invention is prepared using a composition for anti-cancer, reducing anti-cancer side effects and suppressing cancer metastasis, including a cannabis extract as an active ingredient.

A medicament according to yet another exemplary embodiment of the present invention is prepared using a composition for anti-cancer, reducing anti-cancer side effects and suppressing cancer metastasis, including a cannabis extract as an active ingredient.

Hereinafter, the present invention will be described in more detail.

As used herein, the term 'extract' has a meaning commonly used as a crude extract in the art as described above, but also includes a fraction obtained by additionally fractionating an extract in a broad sense. That is, an extract includes not only those obtained using the above-described extraction solvent, but also those obtained by additionally applying a purification process. For example, a fraction obtained by allowing the extract to pass through an ultra-filtration membrane having a predetermined molecular weight cut-off value, and a fraction obtained through various purification methods such as separation by means of various chromatography methods (those manufactured for separation according to the size, charge, and hydrophobicity or hydrophilicity) additionally carried out are included in the extract of the present invention.

To achieve the objects, a composition for anti-cancer, reducing anti-cancer side effects, and suppressing cancer metastasis according to an exemplary embodiment of the present invention includes a cannabis extract as an active ingredient.

Cannabis is an annual plant of the Cannabaceae family, and the subspecies thereof are classified into three subspecies such as *C. sativa* subsp. *sativa*, *C. sativa* subsp. *indica*, and *C. sativa* subsp. *ruderalis*. It is known that cannabis has been widely cultivated for about 12,000 years, mainly in Central Asia, in tropical and temperate regions, when legal regulations had not been applied in the past, and cannabis was used for food in China around 6,000 BC. There is a record of using fiber obtained from cannabis around 4,000 BC, and there is a document in the Chinese herbal book that cannabis was first used for medical purposes in 2,727 BC. However, in the twentieth century, cannabis has been strictly regulated in cultivation and handling not only in Korea but also in most countries due to side effects such as hallucinations. However, the importance of cannabis for its excellent pharmacological action has been increasingly recognized overseas, and there is an increasing movement to permit the use of cannabis for therapeutic purposes. In Korea, studies on cannabis are lacking due to strict regulations on cannabis, and in particular, there have been almost no studies on efficacy verification for medical cannabis and problems on toxicity.

In the past, cannabis was used in various manners depending on the site, and hemp or cannabis leaves as hemp leaves are said to have an action of killing roundworms, and washing hair with water boiled with cannabis leaves is said to causes hair to grow long and shine. Further, cannabis has been used for asthma or prolonged coughing, roundworm, analgesic action, anesthetic, and diuretic. The root of cannabis refers to magen, and was believed to treat difficult delivery and the absence of the placenta, relieve static blood, and alleviate stone strangury, and it was said that as a method of taking the root of cannabis, the root of cannabis was decocted and the decocted water was taken. Mapi as the skin of cannabis was said to treat bruise and heat strangury pain, and mahua as the flower of cannabis was said to be used for treating paralysis and itching. The flower spike of cannabis refers to mafen, and has been utilized for difficult delivery, constipation, gout, madness, insomnia, and the like.

The cannabis extract includes cannabinoids and terpene.

To date, about 400 compounds have been found in cannabis, most of which are cannabinoids, terpenes, and phenolic compounds. Among them, cannabinoids have been known as a representative active ingredient of cannabis, but to date, about 90 kinds of cannabinoids have been revealed, and many ingredients found only in cannabis are also known. Cannabinol (CBN) was separated from cannabis in 1899, but later it was known that cannabinol (CBN) was not a single compound, and after cannabidiol (CBD) and tetrahydrocannabinol (THC), which are pure compounds purified from cannabis, were isolated in the 1930s, studies on ingredients of cannabis became more active.

Efforts to develop drugs using specific ingredients of cannabis have continued, and among them, THC and CBD, the main compounds of medical cannabis have received the most attention for therapeutic purposes. Studies have shown that CBD has no psychotropic effects and is effective in reducing pain and modulating epileptic seizures.

100 or more terpene-based compounds that serve to produce the aroma and taste of cannabis have been identified in cannabis, and are present in the form of various monoterpenoids and sesquiterpenoids. Although terpene has been shown to be associated with various pharmacological effects such as anti-inflammatory effects, studies on terpene compounds extracted from cannabis have been insufficient compared to THC to date.

Terpene is known to exhibit a better effect when acting with cannabinoids such as CBD and THC, and may improve absorption of cannabinoids, overcome bacterial defense mechanisms and minimize side effects.

The cancer includes those selected from the group consisting of thyroid cancer, lung cancer, gastric cancer, liver cancer, colorectal cancer, pancreatic cancer, prostate cancer, uterine cancer, breast cancer, and skin cancer.

Thyroid cancer collectively refers to cancer that occurs in the thyroid gland, and depending on the histological pattern, progenitor cells of cancer and the degree of differentiation, thyroid cancer is divided into papillary thyroid cancer, follicular thyroid cancer, medullary thyroid cancer, undifferentiated thyroid cancer, anaplastic cancer, metastatic thyroid cancer, and the like. The thyroid gland is a butterfly-shaped organ located under the thyroid cartilage and in front of the airway where air passes when a person is breathing, and the thyroid gland functions to produce and store thyroid hormones and deliver the hormones to the organs that require the hormones.

Lung cancer refers to a malignant tumor that arises in the lungs, and originates in the lungs themselves (primary lung cancer), or also occurs when cancer originating from other organs metastasizes to the lungs. The types of primary lung cancer are classified into non-small cell lung cancer and small cell lung cancer based on the size and morphology of the cancer cells, and non-small cell lung cancer accounts for 80 to 85% of lung cancer, which is again divided into glandular cancer (adenocarcinoma), squamous cell carcinoma, large cell carcinoma, and the like. The remaining small cell lung cancers generally have a high grade, and at the time of discovery, most of the small cell lung cancers have already metastasized to other organs, the contralateral lung, and the mediastinum (space between both the lungs where the heart, trachea, esophagus, aorta, and the like are located) through lymphatic vessels or blood vessels.

Gastric cancer is a term that collectively refers to all cancers that originate in the stomach, and gastric adenocarcinoma, which accounts for the majority of gastric cancer, originates from gastric mucosal gland cells (gland cells), and may be further classified into various types depending on how the cells are observed under a microscope. In addition, gastric cancer includes all of the lymphoma originating in lymphoid tissue, interstitial tumor originating in nerves and muscle tissues of the stomach, sarcoma (malignant tumor derived from a non-epithelial tissue), neuroendocrine cancer secreting hormones, and the like.

Liver cancer refers to the tumor primarily originating from the liver, that is, the primary malignant tumor, and the general public commonly also calls cancer that has metastasized from other organs to the liver as liver cancer, but strictly speaking, liver cancer refers only to primary cancer. Pathologically (histologically), there are various types of primary liver cancer such as hepatocellular carcinoma, bile duct epithelial carcinoma, hepatoblastoma, and angiosarcoma, and among them, hepatocellular carcinoma and bile duct epithelial carcinoma make up the majority of primary liver cancer.

The large intestine is divided into the vermiform appendix, the cecum, the colon, the rectum, and the proctodaeum, and colon is again divided into the ascending colon, the transverse colon, the descending colon, and the sigmoid colon, and among them, malignant tumors that occur in the cecum, colon and rectum are called colorectal cancer. Most colorectal cancers refers to glandular cancer (adenocarcinoma), that is, cancer occurring in glandular cells of the mucous membranes, and other primary types such as lymphoma, malignant carcinoid, and leiomyosarcoma may occur.

Pancreatic cancer is a mass (lump) composed of cancer cells occurring in in the pancreas, and 90% or more of pancreatic cancer is glandular cancer in which cancer occurs in glandular cells of the pancreatic duct. There are many types of pancreatic tumors, the most common of which are benign cystic tumors (cystoma), and mesenchymal tumors such as serous and mucinous cystic tumors, intraductal papillary mucinous tumor, solid pseudopapillary tumor, lymphoepithelial cyst, and cystic teratoma belong to the benign cystic tumors. Malignant tumors include neuroendocrine tumors in addition to pancreatic ductal adenocarcinoma and acinar cell carcinoma, which are exocrine tumors. Some cysts are malignant, and those that were initially benign may become malignant.

Prostate cancer is a cancer that originates in the prostate and is mostly adenocarcinoma that originates in prostate cells. Prostate cancer cells continue to proliferate out of normal control, invade other nearby tissues, or metastasize to distant tissues through blood vessels and lymphatic vessels. The types are classified according to the degree of differentiation of tumor tissues and the characteristics of cells. The benign tumor that originates in the prostate is prostatic hyperplasia, and the malignant tumor is called prostate cancer.

Uterine cancer collectively refers to malignant tumor that originates in the uterus, and is divided into cervical cancer and endometrial cancer according to the site of occurrence Cervical cancer and endometrial cancer are carcinomas that completely differ not only in anatomical development site but also in disease causes, symptoms and syndromes, progress aspect, histological characteristics, treatment methods, and the like. Cervical cancer is more common in Korean women, endometrial cancer is more common in Western women, but the incidence rate of endometrial cancer in Korean women is increasing.

Breast cancer is a type of malignant tumor that can spread outside the breasts and be life-threatening, and is divided into cancers that occur in parenchymal tissues such as lactiferous duct and the lobule and cancers that occur in other stromal tissues, depending on the site of occurrence. Lactiferous ductal and lobular cancers are again divided into invasive and non-invasive breast cancers, depending on the extent to which the cancer cells have spread to surrounding tissues. Male breast cancers account for 1% or less of female breast cancers, and invasive ductal carcinoma is most commonly found.

Skin cancer is a cancer that originates in the skin which is the outermost layer of the human body, and skin cancer that originates in the skin from the onset is called primary skin cancer, and skin cancer that originates in other organs and has metastasized to the skin is called metastatic skin cancer. In general, skin cancer refers to only primary skin cancer that originates in the skin from the outset, and refers to only the three most commonly occurring squamous cell carcinoma, basal cell carcinoma, and malignant melanoma in a strict sense. Skin cancers may be broadly divided into malignant melanoma and non-melanoma skin cancer.

The present invention is those that suppress the activity of MMP-2 and MMP-9 to decrease the rate of cancer metastasis and can be used for those that may show an anti-cancer effect, and is not limited to the examples.

The composition shows effects of suppressing terminal cancer metastasis and reducing the viability of cancer cells.

Cancer may be divided into early, advanced, and terminal stages at diagnosis, and the early stage refers to a period when cancer can be completely cured by appropriate treatment and the advanced stage refers to a period when cancer cannot be completely cured, but prolonging life can be expected through aggressive anti-cancer treatment (surgery, radiation therapy, anti-cancer chemotherapy (anti-cancer drug treatment)). In contrast, the terminal stage is a period when such aggressive anti-cancer treatment cannot contribute to the prolonging of life, but rather increases only the risk of side effects, and even chemotherapy, which plays an important role in the treatment of terminal cancer, has been a major obstacle to treatment due to the resistance of cancer to anti-cancer drugs, which occurs during chemotherapy.

In particular, the terminal stage is a step in which cancer has grown beyond a certain size, and is a period when the progression to cancer is promoted by contributing to the growth and metastasis of cancer, evasion of immune mechanism, and the like, and a patient suffers from various symptoms including pain from advanced disease, and pain regulation, dyspnea regulation, and the like using various analgesics are performed.

Thus, in the present invention, as the composition of the present invention is used as a composition for anti-cancer, reducing anti-cancer side effects and suppressing cancer metastasis using a cannabis extract, it is possible to provide a composition as an anti-cancer agent which lowers the occurrence of side effects caused by internal use and administration and does not cause resistance, unlike a chemotherapeutic agent.

More specifically, it is possible to provide a composition which is excellent in effects of treating terminal cancer by including a cannabis extract as an active ingredient to suppress the metastasis of terminal cancer and reduce the viability of cancer cells.

Preferably, the composition for anti-cancer, reducing anti-cancer side effects and suppressing cancer metastasis may further include an *Erigeron annuus* (L.) Pers extract, a *Ceratonia siliqua* (L.) Taub. extract, and a *Stellaria media* extract.

The *Erigeron annuus* (L.) Pers is a native of North America, a biennial grass growing in fields, plains and roadsides in various parts of Korea, and a genus *Chrysanthemum* plant, and various physiological activities thereof such as dyspepsia, malaria, enteritis, hepatitis, diuretic action or hypoglycemic action are known.

The *Ceratonia siliqua* (L.) Taub. is s an evergreen broad-leaved shrub that grows about 10 m in height, and is well tolerated by drought. The leaves contain resin. In the fall, small faint green-brown flowers bloom and long green pods run. The pods, when ripe, turn chocolate-colored and contain small, glossy, hard beans therein. Carob gum, which softens the skin, is popular as a skin pack and is also used to treat diarrhea.

The *Stellaria media* is a biennial herb of the family Caryophyllaceae, grows mainly on a roadside or in an embankment around the end of a field, is about 10 to 20 cm tall, and is rich in minerals such as protein, calcium and iron. The *Stellaria media* strengthens the stomach and intestines, cleanses the blood and improves milk production. The *Stellaria media* may also treat inflammation such as gum disease, tooth decay, appendicitis, enteritis, and bowel ulcers.

However, no studies on the suppression of cancer metastasis using these plants have been reported.

When the natural extracts are used in combination, the effect of suppressing cancer metastasis is enhanced due to the mixing action among the constituent ingredients.

As the *Erigeron annuus* (L.) Pers extract, the *Ceratonia siliqua* (L.) Taub. extract and the *Stellaria media* extract are additionally included, it is possible to provide a composition having excellent preference by neutralizing the taste and aroma peculiar to the cannabis extract.

Preferably, the composition of the present invention may include 20 to 40 parts by weight of the *Erigeron annuus* (L.) Pers extract, 20 to 40 parts by weight of the *Ceratonia siliqua* (L.) Taub. extract, and 20 to 40 parts by weight of the *Stellaria media* extract based on 100 parts by weight of the cannabis extract. When the composition of the present invention is used as a complex extract within the above-range, it is possible to exhibit excellent cancer metastasis suppression and anti-cancer effects and simultaneously provide the composition as a composition having excellent preference.

The cannabis extract includes those that suppress the activity of MMP-2 and MMP-9 to decrease the rate of cancer metastasis.

Matrix metalloproteinase (MMP) is an extracellular matrix degrading enzyme, acts as a regeneration, embryo development, and neovascularization factor in vivo or is used as a protein to suppress the tumor cell apoptosis or activate the growth factors, and is a key enzyme involved in extracellular matrix degradation and cell migration.

Among such MMPs, particularly, MMP-2 and MMP-9 are known to act specifically to type IV collagen and play an important role in cancer invasion and metastasis.

Cancer metastasis and invasion are fundamental characteristics of malignant cancer cells. Cancer invades the blood vessels as well as metastases in the early stage. Cancer cells go through several important steps in the processes of invasion and metastasis. In these processes, the degradation of the extracellular matrix that makes up the basement membrane is an essential early step, because the extracellular matrix surrounding the cancer tissue and the basement membrane are regarded as walls in the invasion of cancer. Various proteolytic enzymes participate in this process and reach the final step through degradation of the extracellular matrix and basement membrane, which are external environmental barriers. However, a proteolytic enzyme secreted from cells is an inactive form of pro-MMP-9, which is activated through a series of enzyme activations, including the production of an active form of plasminogen (plasmin) by a urokinase-type plasminogen activator (uPA). Activated MMP-9 enhances the ability to invade cancer cells.

Thus, the present invention may provide a composition for anti-cancer, reducing anti-cancer side effects and suppressing cancer metastasis, which delays the rate of invasion and metastasis of cancer cells through effects of suppressing the enzymatic activity of MMP-2 and MMP-9 enzymes of a cannabis extract.

The extract includes those extracted using an extraction solvent selected from the group consisting of water, $C_1$ to $C_6$ lower alcohols, and a mixture thereof.

Specifically, in order to prepare a cannabis extract, a natural extract may be obtained by including: grinding a natural product; leaching the ground product by using an organic solvent; leaching a sample, and then drying the sample; re-leaching the dried sample by using an organic solvent; leaching the sample, and then drying the sample; leaching the sample by using water; and leaching the resulting product.

The method of obtaining the natural extract may further include performing fractionation on the natural extract extracted by using the organic solvent by using an organic solvent.

The extraction solvent may be used 2 to 50 times, more specifically 2 to 20 times, based on the weight of the sample. For extraction, the sample may be left to stand in the extraction solvent for leaching for 1 to 72 hour, more specifically, 24 to 48 hours.

The extract may be prepared in a powder state by additional processes such as distillation under reduced pressure and freeze drying or spray drying, and the method include obtaining an extract by an extraction method selected from the group consisting of a solvent extraction method, an ultrasonic extraction method, a reflux extraction method, a leaching method, a fermentation method and a processing method.

The ultrasonic extraction method performs the reaction at 30 to 50° C. for 0.5 to 2.5 hours, and the extraction solvent is obtained from water or a 50 to 100% alcohol having 1 to 6 carbon atoms. Specifically, the extract is extracted at 40 to 50° C. for 1 to 2.5 hours, and an extraction solvent is obtained from water or a 70 to 80% alcohol having 1 to 6 carbon atoms.

The reflux extraction method is performed by 10 to 30 g of a ground material of the natural product based on water and 100 mL of an alcohol having 1 to 6 carbon atoms, a reflux time of 1 to 3 hours, and a 50 to 100% alcohol having 1 to 6 carbon atoms or water. More specifically, the method is performed by 10 to 20 g of a ground material of the natural product based on 100 mL of an alcohol having 1 to 6 carbon atoms or 100 mL of water, 10 to 20 g of a ground material of a natural product, a reflux time of 1 to 2 hours, and a 70 to 90% alcohol having 1 to 4 carbon atoms, or water.

The leaching method is performed at 15 to 30° C. for 24 to 72 hours, and as an extraction solvent, water or a 50 to 100% alcohol having 1 to 6 carbon atoms is used. More specifically, the leaching method is performed at 20 to 25° C. for 30 to 54 hours, and the extraction solvent is obtained by water or a 70 to 80% alcohol having 1 to 6 carbon atoms.

After extraction, the extract may be fractionated by sequentially applying new fractionation solvents. For a fractionation solvent used during the fractionation, the solvent is one or more selected from the group consisting of water, hexane, butanol, ethyl acetic acid, ethyl acetate, methylene chloride, and a mixture thereof, preferably, ethyl acetate or methylene chloride.

A functional food according to another exemplary embodiment of the present invention is prepared using a composition for anti-cancer, reducing anti-cancer side effects and suppressing cancer metastasis, including a cannabis extract as an active ingredient.

"Functional food" as defined herein means a food manufactured and processed using raw materials or ingredients that have functional properties that are useful for the human body according to Act No. 6727 on functional foods, and "functional" is meant to be taken for the purpose of regulating nutrients to the structure and function of the human body, or obtaining effects useful for public health use, such as physiological effects.

A skin external preparation according to still another exemplary embodiment of the present invention is prepared using a composition for anti-cancer, reducing anti-cancer side effects and suppressing cancer metastasis, including a cannabis extract as an active ingredient.

A medicament according to yet another exemplary embodiment of the present invention is prepared using a composition for anti-cancer, reducing anti-cancer side effects and suppressing cancer metastasis, including a cannabis extract as an active ingredient.

A dosage form of the medicament of the present invention may be in a preferred form according to the use method, and in particular, the medicament of the present invention may be formulated using a method publicly known in the art so as to provide a rapid, sustained, or delayed release of an active ingredient after being administered to mammals. Specific examples of the dosage form include granules, powders, syrups, solutions, suspensions, pills, infuses, tablets, suppositories, injections, spirits, capsules, pills, soft or hard gelatin capsules, and the like.

The preferred dose for the medicament of the present invention depends on the condition and body weight, the degree of the disease, the form of drug, the administration route and the duration, but may be appropriately selected by a person having ordinary skill in the art to which the present invention pertains.

According to the composition for anti-cancer, reducing anti-cancer side effects and suppressing cancer metastasis, including the cannabis extract of the present invention as an active ingredient, it is possible to provide a composition for anti-cancer, reducing anti-cancer side effects and suppressing cancer metastasis, which is excellent in an effect of suppressing cancer metastasis, exhibits an effect of reducing the viability of cancer cells, does not have the occurrence of side effects during internal use and administration, and does not cause resistance by suppressing the activity of MMP-2 and MMP-9 enzymes.

DETAILED DESCRIPTION

Hereinafter, the Examples of the present invention will be described in detail such that a person skilled in the art to which the present invention pertains can easily carry out the present invention. However, the present invention can be implemented in various different forms, and is not limited to the Examples described herein.

Preparation Example: Preparation of Extract

Preparation of Cannabis Extract

Cannabis including leaves and flowers was washed thoroughly with running water and then air-dried completely. The dried cannabis was pulverized with a mixer and then prepared as a powder. After 50% ethanol as an extraction solvent was added to the powder sample at a ratio of 1:10 (w:v) and then the powder sample was completely immersed, extraction was performed repeatedly three times at 80° C. under reflux for each 3 hours. The liquid extract was filtered with a Whatman No. 2 filter paper. A cannabis extract (CE) was prepared by concentrating the filtrate at 60° C. under reduced pressure.

2. Preparation of Other Natural Extracts

An *Erigeron annuus* (L.) Pers extract (EE), a *Ceratonia siliqua* (L.) Taub. extract (IE), and a *Stellaria media* extract (SE) were prepared using a method which is the same as the preparation method of the cannabis extract (CE).

3. Preparation of Complex Extract

A complex extract was formed by mixing the cannabis extract (CE), the *Erigeron annuus* (L.) Pers extract (EE), the *Ceratonia siliqua* (L.) Taub. extract (IE), and the *Stellaria media* extract (SE) as shown in the following Table 1.

TABLE 1

|    | MX1 | MX2 | MX3 | MX4 | MX5 | MX6 |
|----|-----|-----|-----|-----|-----|-----|
| CE | 100 | 100 | 100 | 100 | 100 | 100 |
| EE | —   | 10  | 20  | 30  | 40  | 50  |
| IE | —   | 10  | 20  | 30  | 40  | 50  |
| SE | —   | 10  | 50  | 30  | 40  | 50  |

(Unit: parts by weight)

Experimental Example 1: Cytotoxicity Experiments

Toxicity Experiments

In order to test the toxicity of cannabis extract (CE) and complex extracts (MX2 to MX6), differences in toxicity and side effects during the administration of the complex extracts were confirmed in a rat repetitive dose toxicity experiment.

Six-week-old SD male and female rats were divided into 10 per group (5 males and 5 females), and the complex extracts MX1 to MX6 were administered to the groups, and after each drug was dissolved in a 0.5% MC solution, oral administration once daily at the same morning time was repeated for 13 weeks.

As a single dose, the solution was administered in an amount of 3.75 mg/kg to 5 mg/kg. Thereafter, the mortality rate, general symptoms, weight change, and food and water intake were observed.

As a result, no dead individuals occurred during the experimental period. In view of the experimental results, it was confirmed that the cannabis extract (CE), the *Erigeron annuus* (L.) Pers extract (EE), the *Ceratonia siliqua* (L.) Taub. extract (IE), the *Stellaria media* extract (SE), and a mixture thereof had no toxicity problems.

Cancer Cell Viability Experiment 2-1. Cannabis Extract (CE)

The cell viability of HCT116 cells and HT-29 cells as human colorectal cancer cells to which the cannabis extract (CE) was administered was measured.

First, HCT116 cells and HT-29 cells were cultured in a humidified incubator under conditions of an RPMI 1640 (Sigma Chemical CO.) medium including 10% fetal bovine serum (GIBCO), a temperature of 37° C., and 5% CO2/95% air. In this case, the culture medium was replaced once every other day. After confluent growth, the cells were subcultured by trypsin treatment with a 0.25% trypsin-EDTA solution. After the cells were cultured for 4 to 5 days, the cells were aliquoted at a density of $5\times10^4$ cells/well in a 24-well plate, and the medium volume of each well was adjusted to 1 ml.

Thereafter, after the cells were treated with the cannabis extract (CE) prepared in the Preparation Example at concentrations of 0 μm, 10 μm, 20 μm, 30 μm, 40 μm, 50 μm, and 100 μm, respectively and cultured for 24 hours, 100 μl of 3-(4,5-dimethylthiazol-2-yl)-2,5-diphenyl tetrazolium bromide (MTT); 5 g MTT/l in H2O] was added thereto, and then the cells were further cultured for 4 hours, and 200 μl of dimethyl sulfoxide (DMSO) was added to the wells containing each cell and mixed with a pipette in order to dissolve the reduced MTT crystals. The relative cell viability was determined by scanning with a microplate reader (Molecular Devices, Menlo Park, Calif.) with a 540 nm filter.

Figure 1:
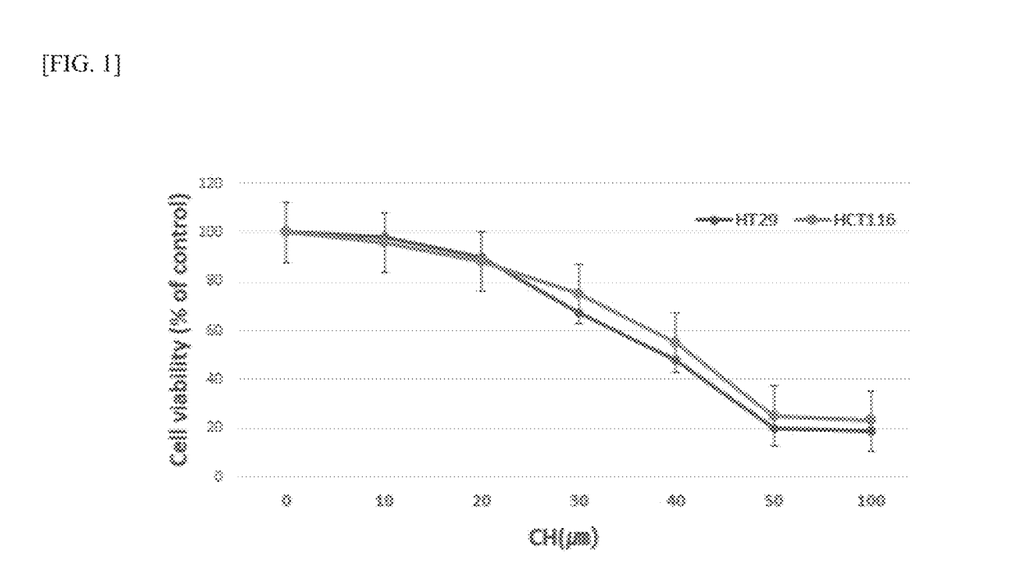
FIG. 1 is an experimental result for the viability of cancer cells of a composition according to an exemplary embodiment of the present invention.

The results thereof are illustrated in FIG. 1, and it was confirmed that the viability of HCT116 cells and HT-29 cells, which are human colorectal cancer cells to which cannabis extract (CE) was administered, was decreased.

In view of the experimental results, it was confirmed that the cannabis extract (CE) was effective for reducing the survival of cancer cells.

2-2. Composite Extract

In order to examine the cancer cell viability of the complex extracts (MX2 to MX6), the same experiment as the cell viability experiment of the cannabis extract (CE) was performed, and the results thereof are shown in comparison with the relative effect on the cannabis extract (CE).

For the viability of cancer cells compared to the cannabis extract (CE), the CE was set at an index of 5, and the cancer cell viability of MX2 to MX6 was evaluated as an index of 1 to 10. It can be said to mean that the higher the index is, the smaller the viability of cancer cells is.

TABLE 2

|  | CE | MX2 | MX3 | MX4 | MX5 | MX6 |
|---|---|---|---|---|---|---|
| Suppression of survival of HCT116 cells | 5 | 6 | 7 | 8 | 7 | 6 |
| Suppression of survival of HT-29 cells | 5 | 5 | 6 | 6 | 6 | 5 |

(Unit: Index)

As shown in Table 2 above, it was confirmed that the complex extracts MX2 to MX6 reduced the viability of cancer cells equivalent to or higher than that of the cannabis extract (CE). This can be said to mean that when the complex extract is used as a natural complex extract, the effect of reducing the viability of cancer cells is excellent due to the complex action of each ingredient, compared to when only the cannabis extract (CE) is used.

Experimental Example 2: Resistance Experiment

Cannabis Extract (CE)

Figure 2:
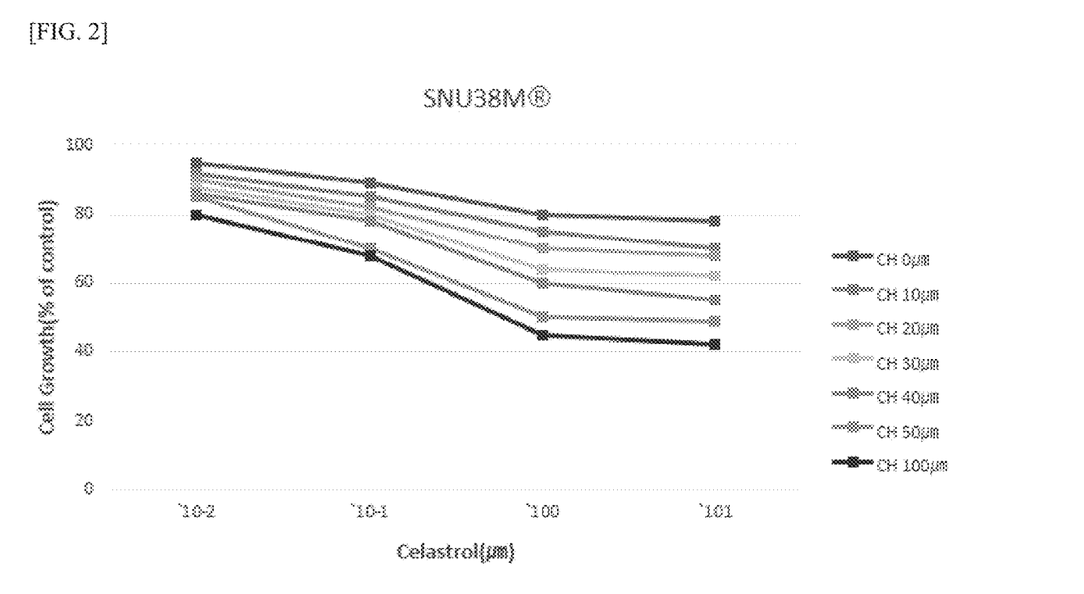
FIG. 2 is an experimental result for the resistance of a cancer cell line SNU38M® to the composition according to an exemplary embodiment of the present invention.
Figure 3:
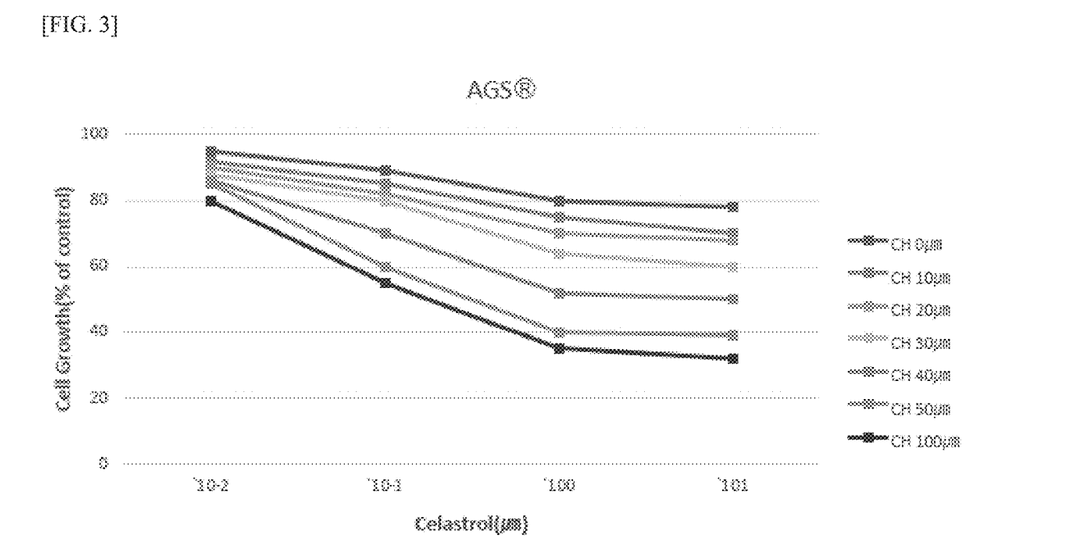
FIG. 3 is an experimental result for the resistance of a cancer cell line AGS® to the composition according to an exemplary embodiment of the present invention.

After the cannabis extract (CE) was injected at a concentration of 0 μm, 10 μm, 20 μm, 30 μm, 40 μm, 50 μm, and 100 μm, respectively into liver cancer and gastric cancer cell lines (SNU38M®, AGS®) showing resistance to celastrol which is an ingredient with anti-cancer action, resistance was analyzed by MTT assay. As a result, as illustrated in FIGS. 2 and 3, it was found that the cannabis extract (CE) suppressed the resistance of each cancer cell line.

Complex Extract

In order to see whether complex extracts (MX2 to MX6) also cause resistance of the cancer cell lines, the same experiment as the resistance experiment of the cannabis extract (CE) was performed, and the results thereof are shown in comparison with the relative effect on cannabis extract (CE).

For the resistance of cancer cell lines compared to the cannabis extract (CE), the CE was set at an index of 5, and the cancer cell line resistance to MX2 to MX6 was evaluated as an index of 1 to 10. It can be said to mean that the larger the index is, the less resistant the cancer cell line is.

TABLE 3

|        | CE | MX2 | MX3 | MX4 | MX5 | MX6 |
|--------|----|-----|-----|-----|-----|-----|
| SNU38M ® | 5  | 6   | 7   | 7   | 7   | 6   |
| AGS ®   | 5  | 5   | 5   | 6   | 7   | 6   |

(Unit: Index)

As shown in Table 3 above, it was confirmed that the complex extracts MX2 to MX6 did not cause resistance of cancer cell lines equivalent to or higher than that of the cannabis extract (CE). This can be said to mean that when the natural complex extract is used, the effect of suppressing the resistance of cancer cell lines is excellent due to the complex action of each ingredient, compared to when only the cannabis extract (CE) is used.

Experimental Example 3: Effect of Suppressing Cancer Metastasis

Cannabis Extract (CE)

In order to investigate the effects of the cannabis extract (CE) on the enzymatic activity of MMP-2 and MMP-2 which are enzymes essential for invasion and neovascularization of cancer cells during cancer metastasis through gelatin degradation of the extracellular matrix, the following experiment was performed.

First, for the activity of MMP-2 and MMP-9, the experiment was performed by treating the colorectal cancer cells HCT116 cells cultured in Experimental Example 1 with the cannabis extract (CE) and treating the HCT116 cells with 1 ng/ml of PMA known to stimulate the expression and activity of MMP-2 and MMP-9.

Figure 4:
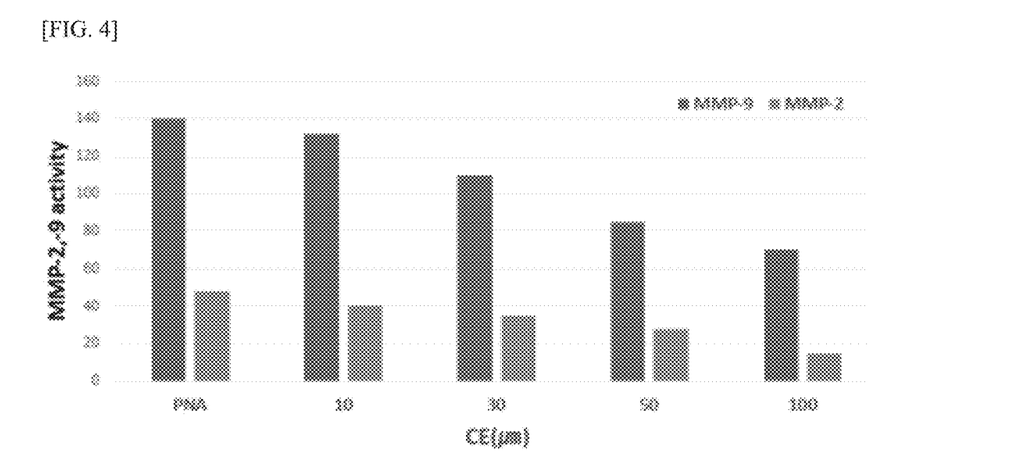
FIG. 4 is an experimental result showing the activity of MMP-2 and MMP-9 enzymes of the composition according to an exemplary embodiment of the present invention.

After HCT116 cells were treated with the cannabis extract (CE), enzymatic activities of MMP-2 and MMP-9 were measured in the supernatant cultured for 72 hours. As in FIG. 4, it was shown that the cannabis extract (CE) reduced the activity of MMP-9 in a concentration-dependent manner at 10 μm or more compared to the PMA-treated group. In addition, it was shown that the activity of MMP-2, which is in an active form, was reduced at a concentration of 30 μm or more, and the activity was reduced by 50% compared to the PMA-treated group at a maximum concentration of 100 μm.

Complex Extract

In order to investigate the effect of suppressing the cancer metastasis of the complex extracts (MX2 to MX6), the same experiment as the experiment of the cannabis extract (CE) was performed, and the results thereof are shown in comparison with the relative effect on cannabis extract (CE).

For the effect of suppressing cancer metastasis compared to the cannabis extract (CE), the CE was set at an index of 5, and the effects of MX2 to MX6 on the suppression of the enzymatic activities of MMP-2 and MMP-9 were evaluated as an index of 1 to 10. It can be said to mean that the higher the index is, the better the effects of suppressing the cancer metastasis are.

TABLE 4

|                              | CE | MX2 | MX3 | MX4 | MX5 | MX6 |
|------------------------------|----|-----|-----|-----|-----|-----|
| Suppression of activity of MMP-2 | 5  | 6   | 7   | 8   | 7   | 6   |
| Suppression of activity of MMP-9 | 5  | 5   | 7   | 7   | 6   | 5   |

(Unit: Index)

As shown in Table 4 above, it was confirmed that the complex extracts MX2 to MX6 suppressed the enzymatic activities of MMP-2 and MMP-9 equivalent to or higher than that of the cannabis extract (CE). This can be said to mean that when the natural complex extract is used, the effect of suppressing the enzymatic activities of MMP-2 and MMP-9 is excellent due to the complex action of each ingredient, compared to when only the cannabis extract (CE) is used.

Experimental Example 4: Preference Test

Sensory Evaluation Test

Tea beverages were prepared by diluting MX1 and the complex extracts MX3 to MX6. The tea beverages were sampled by 10 tasters, and the taste and aroma were expressed by an index of 1 to 10, and the average values (applied to a rounding of 0.5) are shown in the following Table 5. The higher the number of the index is, the higher the preference is.

TABLE 5

|                              | MX1 | MX2 | MX3 | MX4 | MX5 | MX6 |
|------------------------------|-----|-----|-----|-----|-----|-----|
| Taste                        | 6.0 | 6.0 | 6.5 | 7.0 | 7.0 | 6.0 |
| Aroma                        | 6.0 | 6.5 | 6.5 | 7.0 | 7.5 | 7.0 |
| Overall preference (average) | 6.0 | 6.0 | 7.0 | 7.0 | 7.0 | 6.5 |

(Unit: Index)

Referring to Table 5, it can be seen that in the case of MX1, the unique taste and aroma reduced the preference using the cannabis extract alone, and in the case of using the mixture of MX2 to MX6, the preference is enhanced while the taste and aroma peculiar to the cannabis extract are neutralized by other natural extracts. In particular, in the case of using MX3 to MX5, it was confirmed that the aroma was highly evaluated and the preference was also enhanced significantly.

Therefore, in the case of using the complex extracts MX3 to MX5, it is possible to provide a functional food with higher aroma and taste in terms of preference, which has excellent effects of anti-cancer, reducing anti-cancer side effects, and suppressing cancer metastasis.

While preferred embodiments of the present invention have been described in detail hereinabove, it is to be understood that the scope of the present invention is not limited thereto, and various modifications and improvements made by those skilled in the art using basic concepts of the present invention, which are defined in the following claims also fall within the scope of the present invention.

What is claimed is:

1. A method of making a cannabis extract consisting essentially of:
   a) grinding cannabis to form ground cannabis;
   b) extracting the ground cannabis by using a first organic solvent to form a first extracted cannabis extract;
   c) drying the first extracted cannabis extract to form a first dried cannabis product;
   d) extracting the first dried cannabis product by using a second organic solvent to form a second extracted cannabis product;
   e) drying the second extracted cannabis product to form a second dried cannabis product;
   f) extracting the second dried cannabis with water to form a third cannabis extract; and
   g) the third cannabis extract is then processed into a powder by subjecting it to distillation under reduced pressure, freeze drying or spray drying to yield the cannabis extract, wherein the amounts of the first organic solvent and the second organic solvent are 2 times to 50 times greater than the amount of the ground cannabis product and the first dried cannabis product; in each extracting step, each of the ground cannabis product and the first dried cannabis product are left to stand in the first organic solvent and the second organic solvent for 1 hour to 72 hours and wherein the third extract is further consisting essentially of 20 to 40 parts by weight of an Erigeron annuus (L.) Pers extract, 20 to 40 parts by weight of a Ceratonia siliqua (L.) Taub. extract, and 20 to 40 parts by weight of a Stellaria media extract based on 100 parts by weight of the third cannabis extract.

* * * * *